United States Patent [19] [11] 4,039,593
Kamienski et al. [45] Aug. 2, 1977

[54] PREPARATION OF HYDROXY-TERMINATED CONJUGATED DIENE POLYMERS

[75] Inventors: Conrad W. Kamienski; Robert C. Morrison, both of Gastonia, N.C.

[73] Assignee: Lithium Corporation of America, Gastonia, N.C.

[21] Appl. No.: 728,233

[22] Filed: Sept. 30, 1976

Related U.S. Application Data

[63] Continuation-in-part of Ser. No. 481,554, June 21, 1974, abandoned, which is a continuation-in-part of Ser. No. 361,467, May 18, 1973, Pat. No. 3,954,894.

[51] Int. Cl.$^2$ .................... C07C 29/00; C07C 43/14; C07C 33/06; C07C 33/10
[52] U.S. Cl. .............................. 260/635 E; 260/575; 260/613 D; 260/615 R; 260/618 F; 260/618 R; 260/633; 526/55

[58] Field of Search ............... 260/635 E, 575, 613 D, 260/615 R, 618 R, 618 F, 633; 526/55

[56] References Cited

U.S. PATENT DOCUMENTS

| | | | |
|---|---|---|---|
| 3,055,952 | 9/1962 | Goldberg | 260/635 E |
| 3,468,972 | 9/1969 | Hsieh | 526/55 |
| 3,598,793 | 8/1971 | Koch | 260/665 R |

Primary Examiner—Joseph E. Evans
Attorney, Agent, or Firm—Wallenstein, Spangenberg, Hattis & Strampel

[57] ABSTRACT

Preparation of hydroxy-terminated conjugated diene polymers, particularly polybutadienes, by capping of organodilithium- and organopolylithium- terminated conjugated diene polymers or polybutadienes with lower alkylene oxide or epoxide capping agents in the presence of certain potentiating agents or catalysts exemplified particularly by small proportions of N,N,N$^1$,N$^1$-tetramethylenediamine (TMEDA).

22 Claims, No Drawings

PREPARATION OF HYDROXY-TERMINATED CONJUGATED DIENE POLYMERS

This application is a continuation-in-part of application Ser. No. 481,554, filed June 21, 1974, which is, in turn, a continuation-in-part of application Ser. No. 361,467, filed May 18, 1973, now U.S. Pat. No. 3,954,894, dated May 4, 1976.

The reaction between lower alkylene oxide or epoxide capping agents as, for example, ethylene oxide or propylene oxide, and living di- and multilithio-terminated polybutadienes (HTPB) is not 100% complete to form the desired hydroxyl grouping. A major reason for low capping efficiency is due to the molecular association of polymer chains. As the capping agent is introduced, a hard gel usually forms due to association between the newly formed C-O-Li species and the unreacted C-Li species. Due to the gel, the remaining uncapped C-Li species thus becomes inaccessible to the capping agent and decreases the capping reaction rate. Such a decreased capping rate allows for the occurrence of side reactions involving the uncapped C-Li species. Among these side reactions are metalation of the capping agent and cleavage of Lewis base, for instance, tetrahydrofuran (THF), in which the capping reaction is commonly carried out, causing a loss of the C-Li species, thereby lowering the capping efficiency. As may be noted from the following TABLE I, the addition of an equivalent of a strong Lewis base, exemplified by THF, to the carbon-lithium terminated polymer, prior to capping, does not improve capping efficiency but serves fundamentally only to reduce the viscosity of the polymer solution prior to the introduction of the capping agent.

It has been discovered, in accordance with our present invention, that the carrying out of the capping reaction in the presence of small proportions, for instance, even as low as almost trace amounts, of certain tertiary amines, most desirably aliphatic tertiary amines, exemplified particularly by N,N,N¹,N¹-tetramethylethylenediamine (TMEDA), significantly increases capping efficiency. This may be achieved in the presence or in the absence of strong Lewis bases such as THF, or other ethers such as methyl ether, ethyl ether or 1,4-dioxane, although, in general, in certain cases it may be desirable to carry out the capping reaction in the presence of such strong Lewis bases in conjunction with the tertiary amines such as TMEDA. Thus, as shown in said TABLE I, wherein a difunctional organolithium initiator was employed in conjunction with small or catalytic amounts of TMEDA in the capping reaction to produce six illustrative hydroxy-terminated conjugated diene polymers or polybutadienes, an average of about a 7% increase in capping efficiency was obtained in contrast to the same capping reaction but where TMEDA was not employed. In TABLE II, in the case of the production of eleven illustrative hydroxy-terminated conjugated diene polymers or polybutadienes, wherein a trifunctional organolithium initiator, or a mixture of di- and trifunctional organolithium initiators, was employed in conjunction with small or catalytic amounts of TMEDA in the capping reaction, in which said polymers had a functionality greater than 2, capping efficiencies are shown averaging about 10% higher than where TMEDA was not employed.

TABLE I
CAPPING EFFICIENCY OF ORGANODILITHIUM-INITIATED HTPB

| Run Co. | $\overline{M}_n$ | OH No. meq/g Theory | OH No. meq/g Found | CLi/ THF | CLi/ TMEDA | (f)* Theory | (f)* Found | Capping Efficiency (%) OH (Found) / OH (Theory) |
|---|---|---|---|---|---|---|---|---|
| 2995 | 4900 | .40 | .34 | 1 | None | 2.0 | 1.67 | 85 |
| 2990 | 5400 | .40 | .35 | 1 | None | 2.0 | 1.89 | 87 |
| 2974 | 2200 | 1.0 | .83 | 1 | None | 2.0 | 1.83 | 83 |
| | | | | | | | | Avg. 85 |
| 3072 | 8700 | .25 | .23 | 1 | 52 | 2.0 | 2.0 | 92 |
| 3095 | 8000 | .29 | .27 | 1 | 52 | 2.0 | 2.16 | 90 |
| 3107 | 7500 | .30 | .28 | 1 | 52 | 2.0 | 2.08 | 92 |
| | | | | | | | | Avg. 92 |

*(f) = functionality

TABLE II
CAPPING EFFICIENCY OF HTPB OF FUNCTIONALITY GREATER THAN TWO

| Run No. | $\overline{M}_n$ | OH No. meq/g Theory | OH No. meq/g Found | C-LI/ THF | C-Li/ TMEDA | Theory | Found | Capping Efficiency (%) OH (Found) / OH (Theory) |
|---|---|---|---|---|---|---|---|---|
| 3015 | 5500 | .60 | .41 | 1 | None | 3.00 | 2.18 | 73 |
| 3029 | 2300 | 1.50 | 1.10 | 1 | None | 3.00 | 2.53 | 73 |
| 3038 | 4900 | .58 | .44 | 1 | None | 2.87 | 2.16 | 75 |
| 3033 | 2250 | 1.37 | .98 | 1 | None | 2.73 | 2.20 | 77 |
| 3073 | 5800 | .48 | .35 | 1 | None | 2.43 | 2.09 | 74 |
| 3010 | 8000 | .27 | .23 | 1 | None | 2.20 | 1.84 | 84 |
| 3014 | 5600 | .40 | .33 | 1 | None | 2.20 | 1.84 | 84 |
| | | | | | | | | Avg. 77 |
| 3046 | 5000 | .60 | .51 | 1 | 52 | 3.0 | 2.50 | 84 |
| 3050 | 7100 | .37 | .34 | 1 | 52 | 3.0 | 2.41 | 91 |
| 3059 | 6200 | .40 | .34 | 1 | 52 | 2.4 | 2.10 | 88 |
| 3057 | 5100 | .47 | .41 | 1 | 52 | 2.35 | 2.08 | 88 |
| | | | | | | | | Avg. 88 |

It may also be noted, in this general connection, that the higher the functionality generally, the lower the capping efficiency, as is more particularly indicated in the attached drawing. Thus, as there shown, the two capping efficiency lines, one with and one without TMEDA, diverge as the functionality is increased from 2.0 to 3.0, thereby indicating that TMEDA plays a greater role in increasing capping efficiencies of hydroxyterminated polybutadienes having a functionality in excess of 2.

While TMEDA is especially efficacious in the practice of our present invention, certain other tertiary amines which can be utilized in place of or in conjunction with TMEDA are azaoxa-alkanes, aza-alkyloxacycloalkanes or oxa-alkylazacycloalkanes of the formulas:

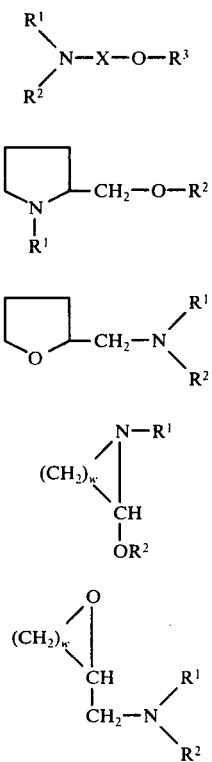

where $R^1$, $R^2$, and $R^3$ are the same or different alkyls each containing from 1 to 4 carbon atoms, namely methyl, ethyl, n-propyl, isopropyl, n-buytl, isobutyl; X is a group such as

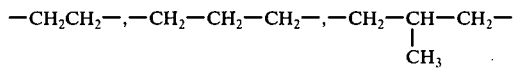

or other divalent aliphatic hydrocarbon or alkylene radical, preferably containing from 2 to 4 carbon atoms; and w is 1 to 4. Illustrative example include, for instance, 2-dimethylaminoethylmethylether [$(CH_3)_2$-N-$CH_2$-$CH_2$-$OCH_3$]; 2-dimethylaminoethylmethyl ether [$(C_2H_5)_2$-N-$CH_2$-$CH_2$-$OCH_3$]; and 2-dimethylamino propylmethyl ether [$(CH_3)_2$-N-$CH_2$-$CH_2$-$CH_2$-$OCH_3$].

Additional tertiary amines which can be utilized in place of or in conjunction with TMEDA in the practice of our present invention are those which have the formulae and various of which are shown in U.S. Pat. No. 3,451,988:

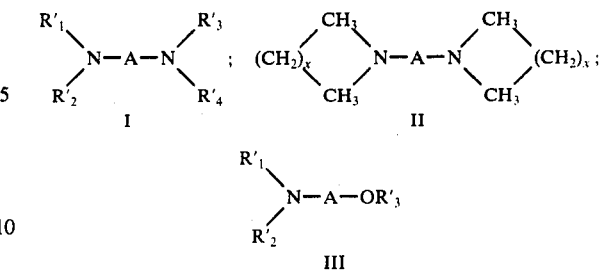

wherein $R'_1$, $R'_2$, $R'_3$ and $R'_4$ are the same or different alkyl radicals of 1 to 4 carbon atoms, inclusive; A, is a non-reactive group; and x is an integer from 0 to 3, inclusive. A in the formulas, is selected from the group consisting of: (1) cycloaliphatic and aromatic radicals and their lower alkyl derivatives having ring structures containing 5 to 7 members, wherein said radicals are attached to the nitrogen atoms at adjacent positions on the rings; illustrative examples include N,N,N',N'-tetramethyl-1, 2-cyclopentanediamine, N,N,N',N'-tetramethyl-1, 2-cyclohexanediamine, N,N,N',N'-tetramethyl-o-phenylenediamine, and 4-ethyl-N,N,N',N'-tetramethyl-o-phenylenediamine, and the like; (2) a monoethylenic radical, said radical containing 0 to 2 monovalent hydrocarbon radicals of 1 to 8 carbon atoms; illustrative examples include N,N,N',N',-tetramethyl-1,2-diaminoethylene, N,N,N',N'-tetramethyl-3,4-diaminohexene-3, and the like; and (3) 1 to 4 methylenic radicals, inclusive, wherein each methylenic radical contains 0 to 2 monovalent hydrocarbon radicals of 1 to 6 carbon atoms; suitable examples include 1,2-dipiperidyl ethane, N,N'-dimethyl-N,N'-diethyl-1,2-ethanediamine, N,N,N',N'-tetramethyl-1-phenyl-1,2-ethanediamine, N,N,N',N'-tetramethyl-1,2-pentanediamine, N,N,N',N'-tetramethyl-1,2-propanediamine, N,N,N',N'-tetramethyl-2, 3-butanediamine, and N,N,N',N'-tetramethyl-1,4-butanediamine.

Particularly useful are diamines having the formula:

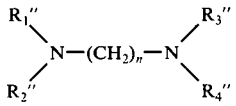

wherein $R_1''$, $R_2''$, $R_3''$ and $R_4''$ are the same or different alkyl radicals of 1 to 3 carbon atoms, inclusive, and n is an integer between 1 and 4, inclusive; illustrative examples include: N,N,N', N'-tetramethylmethanediamine, N,N-dimethyl-N',N'-diethyl-1,2-ethanediamine, N,N,N',N'-tetramethyl-1,2-ethanediamine, N,N,N',N'-tetraethyl-1,2-ethanediamine, N,N,N',N'-tetramethyl-1,3-propanediamine, and N,N,N',N'-tetramethyl-1,4-butanediamine, and the like.

In general, the tertiary amines which function as potentiating agents or catalysts in the capping step are those which contain from 2 to 4 nitrogen atoms separated from each other by saturated aliphatic or cycloaliphatic hydrocarbon groups containing at least 2, and generally from 2 to 8, carbon atoms, the aliphatic groups including, for instance, such groups as

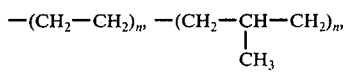

where n is from 1 to 4, and where the aforementioned cycloaliphatic hydrocarbon groups include, by way of example, cyclobutane, cyclopentane, cyclohexane and cyclooctane; and those tertiary amines which contain nitrogen and oxygen which are linked through aliphatic hydrocarbon groups of one or two or more carbon atoms or through cycloaliphatic groups such as those referred to above. In the particularly preferred tertiary amines, the number of carbon atoms will generally range from 4 to 18. Such tertiary amines are well known in the art and include, in addition to those otherwise specifically disclosed herein, such tertiary amines as

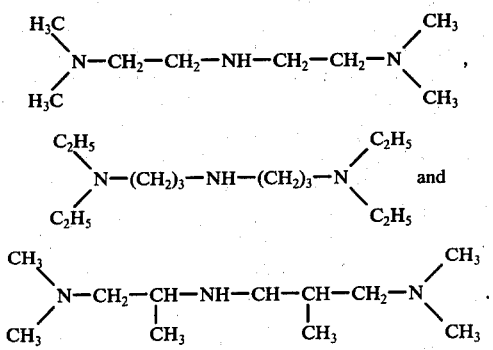

The temperatures at which the capping reaction with the lower alkylene oxides are carried out are per se well known to the art and no novelty is asserted therein. In general, and as is well known, such capping reactions are carried out at low temperatures, commonly at $-30°$ up to about $0°$ C, very commonly in the range of about $-20$ to about $-5°$ C, but such capping operations can also be carried out at much lower temperatures if desired as, for example, at $-60°$ C or $-80°$ C.

The polymerization initiators which are utilized in the production of the intermediate conjugated diene polymers or polybutadienes, prior to the capping reaction, are organopolylithiums (which term is used to include organodilithiums), particularly organotrilithiums, or mixtures of organodilithiums and organotrilithiums. Organodilithium polymerization initiators and organotrilithium polymerization initiators are, broadly, well-known to the art, illustrative examples of organodilithiums being disclosed in our U.S. Pat. No. 3,668,263, and certain of the trilithiums being disclosed, for instance, in U.S. Pat. No. 3,377,404. Particularly advantageous are the types of organotrilithium initiators which are disclosed in our aforementioned U.S. Pat. No. 3,954,894. These latter organotrilithium initiators are soluble in hydrocarbon solvents such as normally liquid alkanes and cycloalkanes such as n-pentane, n-hexane, n-heptane and cyclohexane and normally liquid aromatic hydrocarbons, such as benzene, toluene, xylene, ethylbenzene and pseudocumene, as well as various mixtures of these types. The concentration range of the organotrilithium as prepared in solution can be varied widely, with solutions containing between 0.5 and 2 equivalents of C-Li per liter being generally most desirable.

As disclosed in our aforementioned U.S. Pat. No. 3,954,894, those organotrilithium polymerizaton initiators thereof which can be utilized in the intermediate step of producing the conjugated diene polymers or polybutadienes, prior to the capping operation, are made by mono-adducting a disubstituted vinylic aromatic compound, for instance, a divinyl benzene or a diisopropenyl benzene, with an organo mono-lithium compound, for instance, an alkyllithium such as sec-butyllithium, to form a mono-adduct, and then reacting said mono-adduct with an organodilithium compound to form the desired organotrilithium compound in solution. Alternatively, but less preferably, the disubstituted vinylic aromatic compound can be mono-adducted with the organodilithium compound and the resulting mono-adduct is then reacted with alkyllithium.

In the production of the initial mono-adduct, used in preparing the organotrilithium initiators, various disubstituted vinylic aromatic compounds can be utilized, illustrative of which are 1,3-divinylbenzene; 1,4-divinylbenzene; 1,3-dipropenylbenzene; 1,3-diisopropenylbenzene; 1,4-diisopropenylbenzene; 2,4-diisopropenyltoluene; 2,4-divinyltoluene; the various divinylnaphthalenes; the various diisopropenylnaphthalenes; 1,3-distyrylbenzene; 1,4-distyrylbenzene; 1,2-distyrylbenzene; 1,3-diisobutenylbenzene; and 1,3-diisopentenylbenzene; and said disubstituted vinylic aromatic compounds are reacted with generally $C_2$-$C_{12}$ alkyllithium compounds as, for example, ethyllithium, n-propyllithium, isopropyllithium, n-butyllithium, isobutyllithium, sec-butyllithium tert-butyllithium, n-amyllithium, isoamyllithium, sec-amyllithium, and tert-amyllithium, or substituted alkyllithiums such as aralkyllithiums as, for instance, benzyllithium, 1-lithioethylbenzene and 1-lithio-3-methylpentylbenzene, particularly satisfactory being secondary and tertiary alkyllithiums such as isopropyllithium, sec-butyllithium, tert butyllithium, sec-amyllithium, and tert-amyllithium, said unsubstituted and substituted alkyllithium compounds being, for convenience, all characterized as "alkyllithium" compounds.

In carrying out the initial preparation of the monoadduct, for instance from the disubstituted vinylic aromatic hydrocarbon and the alkyllithium compound, the reaction medium may or may not include tertiary amines, notably monoamines. In the production of the organodilithium compound, and also in the subsequent step of reacting the mono-adduct with the organodilithium compound, tertiary amines should be present. The proportions of such amines, when utilized, are reasonably variable. Thus, it is desirable that said amines be present in proportions in a molar ratio range, based on C-Li, of about 0.5 to 1 to about 4 to 1, with a range of about 1 to 1 being most desirable, and a range higher than 1 to 1 being generally unnecessary. Triethylamine is especially satisfactory but various other tertiary amines, particularly monoamines, can be used as, for example, trimethylamine, tri-n-propylamine, triisopropylamine, ethyl di-n-propylamine, diethyl-n-butylamine, triisobutylamine, TMEDA; and arylalkyl tertiary amines illustrative of which are dimethylaniline, diethylaniline, diisopropylaniline and methylisobutylaniline.

As has been indicated from the foregoing descriptions, the mono addition of an alkyllithium compound to, for instance, a divinyl-substituted aromatic compound can be controlled to give exclusively, or essentially exclusively, a mono adduct, leaving intact one unreacted vinyl grouping which is then reacted with an organodilithium compound to give the hydrocarbon-soluble trifunctonal initiators which can be used in the practice of our invention. Thus, for example, the addition of 1 molar equivalent of 1,3-diisopropenylbenzene to sec-butyllithium in hexane solution yields the mono adduct, shown below:

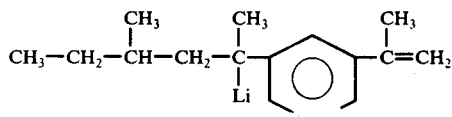

The organodilithium compounds, with which the aforesaid initial mono-adducts are reacted to produce said organotrilithium initiators, include, by way of illustration and among others, 1,3- and 1,4-bis-(1-lithio-3-methylpentyl) benzene, 1,3- and 1,4-bis-(1-lithio-1,3-dimethylpentyl) benzene, and the dilithio dimers of conjugated dienes such as isoprene, 1,4-hexadiene, 1,3-butadiene, 2,5-dimethyl-2,5-hexadiene, 2,3-dimethyl-1,3-butadiene, 1,3-pentadiene (piperylene), 2-methyl-3-ethyl-1,3-butadiene, and the like; as well as the $\alpha\omega$-dilithioalkanes, such as 1,4-dilithiobutane, 1,5-dilithiopentane and the like. Thus, for example, where the monoadduct corresponds to the formula

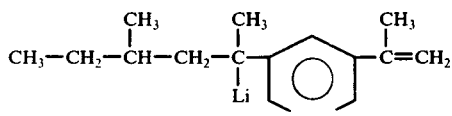

and the organodilithium compound is for example, bis-(1lithio-1,3-dimethylpentyl) benzene (formed by the addition of 1,3-diisopropenylbenzene to 2 molar equivalents of sec-butyllithium), and said organodilithium compound is added to the above monoadduct solution, the resulting organotrilithium compound is shown below:

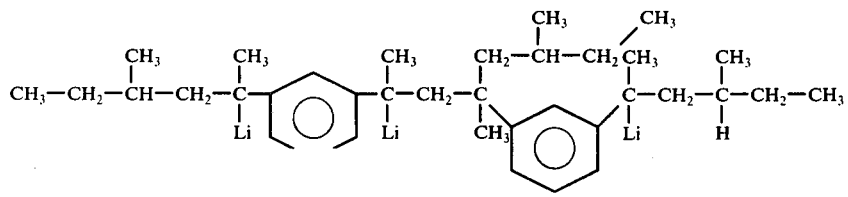

Reaction temperatures utilized in the production of the aforesaid particularly preferred initiators used in the practice of our present invention are variable but, generally speaking, low temperatures are used, usually in the range of about $-60°$ C to not substantially in excess of ambient temperatures, particularly desirably being temperatures in the range of about $-30°$ C to $0°$ C.

The monomers which can be polymerized in the presence of the organodilithium and organopolylithium polymerization initiators are conjugated dienes containing from 4 to 12 carbon atoms, preferably 4 to 8 carbon atoms per molecule. Examples of these conjugated dienes include the following: 1,3-butadiene; isoprene; 2,3-dimethyl-1,3-butadiene; 1,3-pentadiene (piperylene); 2-methyl-3-ethyl-1,3-butadiene; 3-methyl-1,3-pentadiene; 1,3-hexadiene; 2-methyl-1,3-hexadiene, and 3-butyl-1,3-octadiene. In addition, the above conjugated dienes containing various substituents along the chain can also be employed, as, for example, halogenated and alkoxy-substituted dienes such as chloroprene, fluoroprene; 2-methoxy-1,3-butadiene; 2-ethoxy-3-ethyl-1,3-butadiene and the like. Of the conjugated dienes, the especially preferred monomer is 1,3-butadiene, with isoprene and piperylene also being especially suitable. The conjugated dienes can be polymerized alone or in admixture with each other to form copolymers or by charging the dienes sequentially to form block copolymers.

In addition to the above-named conjugated dienes, other monomers can be copolymerized with these dienes including, by way of illustration, vinyl-substituted aromatic compounds such as styrene; 1-vinylnaphthalene; 2-vinyl naphthalene; and alkylcycloalkyl, aryl, alkaryl, alkoxy, aryloxy and dialkylamino derivatives thereof in which the total number of carbon atoms in the combined substituents is generally not greater than 12. Examples of such derivatives include 3-vinyltoluene; 4-phenylstyrene; 4-cyclohexylstyrene; 4p-tolylstyrene; 3,5-diphenylstyrene; 4-methoxystyrene; 4-dimethylamino-styrene; 3,5-diethylaminostyrene; 3-ethyl-1-naphthalene; 6-cyclohexyl-1-vinyl-naphthalene; 6-benzyl-2-vinylnaphthalene; 4-methoxy-1-vinylnaphthalene; 6-phenoxy-1-vinylnaphthalene and the like. The vinyl substituted aromatic compounds can be copolymerized with the conjugated dienes to form random or block copolymers. Generally, the presence, in the polymerization reaction medium, of trialkylamines, dialkylanilines, diarylethers and alkylarylethers in limited amount does not unduly affect the microstructure of the resulting polydiene polymers as does the presence of simple alkyl or cycloalkyl ethers such as diethyl ether or methyl cyclohexyl ether.

The conjugated diene polymers and copolymers which are utilized in the practice of our invention prior to the capping operation may have molecular weights in the range of about 500 to about 100,000, preferably in the range of about 1,000 to about 15,000 and, better still, about 2,000 to 12,000, especially in the case of the polybutadienes.

In the practice of our invention, a suitable capping agent, such as ethylene oxide, is added to the "living" polymer solution, as depicted illustratively in the equations as shown below:

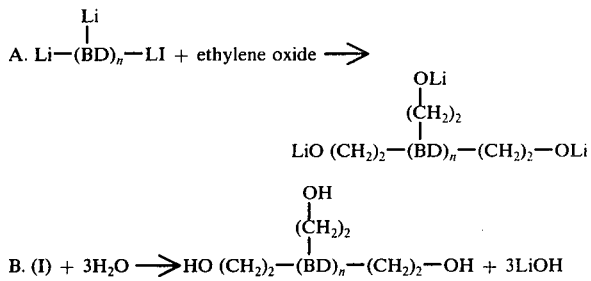

This is done, as pointed out above, in the presence of small or catalytic amounts of TMEDA or similarly acting tertiary amines, illustratively from about 0.01 to 0.1, advantageously from about b 0.015 to 0.025 moles per gram atom of lithium.

In the HTPB, each hydroxy linkage is attached to its own butadiene chain in a star-shaped configuration:

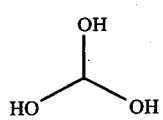

Such HTPB differs from other so-called trifunctional HTPB, which can be made via metalation of difunctional chains (prior to capping with ethylene oxide) in the presence of a strong Lewis base such as THF and a metalating agent such as sec-butyllithium.

The foregoing metalation is non-selective and occurs randomly among the chains yielding chains of varying functionality, i.e., 1, 2, 3, 4 and on up, but having an average functionality of 3. HTPB containing chains of both di- and trifunctionality also can be prepared from a mixture of the aforementioned trilithium initiators and known dilithium initiators. Suprisingly, gel permeation chromatography (GPC) traces of such HTPB generally show the molecular weight distribution to be very narrow, e.g. (MWD=1.13). This MWD is comparable to MWD's of HTPB prepared either with the said trilithium initiators or a conventional dilithium initiator. Also, the predetermined molecular weights (e.g. $\overline{M}_n=5500$) agree with the found molecular weight (e.g. $\overline{M}_n=5600$) calculated for the mixed system. Where mixtures of trilithium initiators and dilithium initiators are utilized in preparing HTPB, the weight ratios of the trilithium to dilithium initiators will generally fall within the range of 90 to 10 to 10 to 90, and more particularly desirable about 65 to 35 to about 35 to 65.

The conjugated diene polymers or polybutadienes containing active carbon-lithium bonds can be capped with lower alkylene oxide or epoxide capping agents which convert these active carbon-lithium bonds to produce hydroxy-terminated polymers. Illustrative examples of these capping agents are ethylene oxide, propylene oxide, butylene oxide, amylene oxide, and hexylene oxide. Especially satisfactory is ethylene oxide.

The following examples are illustrative but in no way limitative of our invention since changes can be made, among other things, in the nature of the conjugated diene utilized, the organolithium polymerization initiator, the hydrocarbon solvent, the capping agent, the proportions of ingredients, temperatures, etc., in light of the guiding principles and teachings contained herein. Examples 1–5 show the preparation of organotrilithium polymerization initiators, and mixtures of organotrilithium and organodilithium initiators, disclosed in said U.S. Pat. No. 3,954,894, which are particularly useful in connection with the carrying out of our present invention. Examples 6–14 show the preparation of conjugated diene polymers or polybutadienes capped pursuant to our present invention. All temperatures recited are in degrees Centigrade.

EXAMPLE 1

Preparaton of an Organotrilithium Initiator Composition via Interaction of 1,3-bis-(1-lithio-1,3-dimethylpentyl)benzene and 3-(1-lithio-1,3-dimethylpentyl)-alphamethylstyrene a. Preparation of 1,3-bis-(1-lithio-1,3-dimethylpentyl)benzene 3330 ml of 1.2N sec-butyllithium in hexane (4 moles) and 404g of triethylamine (TEA) (4 moles) are charged to a 5-liter, 3-neck, round-bottom reaction flask. The reaction flask is equipped with stirrer, thermometer, addition funnel and a dry ice-hexane cooling bath. The flask and contents are cooled to −20° and a premixed solution of DIPB (316g — 2 moles) and 400 ml benzene are added dropwise over a period of 2 hours. The flask and contents are warmed to 30° and stirred for 1 hour.

b. Preparation of 3-(1-lithio-1,3-dimethylpentyl)-alphamethylstyrene 316g (2 moles) of 1,3-diisopropenyl benzene (DIPB) and 400 ml benzene are charged to a dry, argon flushed, 12-liter 3-neck, round-bottom reaction flask. The reaction flask is equipped with a stirrer, thermometer, addition funnel and a dry ice-hexane cooling bath. The flask and contents are cooled to −20° and a premixed solution of 1670 ml of a 1.2N sec-butyllithium in hexane (2 moles) and 202g of TEA (2 moles) are added dropwise over a period of 2 hours. The temperature is held between −20° and −5° throughout the sec-butyllithium-TEA addition.

c. Preparation of Organotrilithium Initiator Composition

The dilithium component of part (a) is added to the cold (−20°) monolithium adduct of part (b). The 12-liter flask and contents are then allowed to warm to ambient temperature. Stirring is continued for 12 hours. A volume of 7260 ml of a clear, deep red solution is obtained as the final product. The total alkalinity content is 0.825N, while the active carbon-lithium content is 0.825N (100% carbon-lithium active product). Gas chromatography analysis shows no sec-butyllithium or diisopropenylbenzene remaining in the solution. The product solution can be used directly as an initiator for the polymerization of conjugated dienes such as 1,3-butadiene.

EXAMPLE 2

Preparation of a Mixed Organodi- and Trilithium Initiator Composition

EXAMPLE 1 is repeated except that the quantity of secbutyllithium used is 0.296 moles in preparing the mono-adduct of part (b), and 1.6 moles each of sec-butyllithium and TEA, and 0.8 moles of DIPB are used to prepare the organodilithium compound of part (a). When completed, the initiator consists of a 64:36 mole % mixture of di- and triorganolithium compounds. A volume of 2205 ml of a clear, deep red solution is obtained as the final product. The total alkalinity content is 0.86N, while the active carbon-lithium content is also 0.86N (100% carbonlithium active product). Gas chromatography analysis shows no sec-butyllithium or diisopropenyl benzene remaining in solution. The product solution can be used directly as an initiator for the polymerization of conjugated dienes such as 1,3-butadiene.

EXAMPLE 3

Preparation of an Organotrilithium Initiator Composition via Interaction of Dilithio Isoprene Dimer and 3-(1-lithio-1,3-dimethylpentyl)-alphamethylstyrene EXAMPLE 1 (b) is repeated except that 0.58 moles each of sec-butyllithium, 1,3-diisopropenyl benzene, and TEA are used in preparing the mono adduct. A volume of 1290 ml of a 0.9N (active) DiLi-1 (dilithio-isoprene-dimer) solution in benzene is added to the mono-adduct above and the reaction mixture stirred overnight. A volume of 2029 ml of a clear, deep red solution is obtained as the final product. The total alkalinity content is 0.86N while the active carbon-lithium content is 0.85N (99% carbon-lithium lithium active product). Gas chromatography analysis shows no sec-butyllithium, DIPB or DiLi-1 remaining in solution. The product solution can be used directly as an initiator for the polymerization of conjugated dienes such as 1,3-butadiene.

EXAMPLE 4

Preparation of an Organotrilithium Initiator Composition via Interaction of 1,3-bis-(1-lithio-3-methylpentyl)benzene and 3-(1-lithio-3-methylpentyl)styrene EXAMPLE 1 is repeated except that 0.492 moles each of 1,3-divinylbenzene (DVB) and sec-butyllithium are used to prepare the mono-adduct. No TEA is used in this step. Also, 0.984 moles each of sec-butyllithium and TEA along with 0.492 moles DVB are used to prepare the diadduct (organodilithium compound). A volume of 1622 ml of a clear, deep red solution is obtained as the final product. The total alkalinity content is 0.91N, while the active carbon-lithium content is 0.9N(99% carbon-lithium active product). Gas chromatography analysis shows no secbutyllithium or DVB remaining in solution. The product solution can be used directly as an initiator for the polymerization of conjugated dienes such as 1,3-butadiene.

EXAMPLE 5

Preparation of an Organotrilithium Initiator Composition via a Sequential Interaction of 1,3-Diisopropenylbenzene with 1,3-bis-(1-lithio-1,3-dimethylpentyl)benzene and Then sec-Butyllithium To 2 moles of 1,3-bis-(1-lithio-1,3-dimethylpentyl) benzene, prepared as in EXAMPLE 1(a) above, is slowly added over a period of 2 hours at $-20°$ a premixed solution of 1,3-diiso-propenylbenzene (316g - 2 moles) and 400 ml of benzene in a 12-liter flask. The mixture is stirred further for a period of 1 to 2 hours at $-20°$ and then a premixed solution of 1670 ml of a 1.2N sec-butyllithium in hexane (2 moles) and 202g of TEA (2 moles) are added dropwise over a period of 2 hours. The temperature is held between $-20°$ and $-5°$ throughout the sec-butyllithium-TEA addition, after which the flask and contents are allowed to warm to ambient temperature. Stirring is continued for 12 hours to insure complete reaction. The total alkalinity and active carbon-lithium contents are essentially equal at 0.83N.

EXAMPLE 6

Preparation of a Hydroxy-Terminated Polybutadiene (HTPB) Employing a Difunctional Lithium Initiator and TMEDA as Capping Catalyst 22.4 liters of cyclohexane and 3632 g of 1,3-butadiene are charged to a 10-gallon polymerization reactor. The initiator (1070 ml of a 0.89N solution of the diadduct of sec-butyllithium and meta-diisopropenylbenzene (DiLi-DIPB) in hexane) are then added to the reactor. After 24 hours, the polymerization of butadiene is considered complete. The reactor and contents are cooled to $-10°$ and 68.4g THF (0.95 moles) along with 2.12g (0.183 moles) of N,N,N',N'-tetramethylethylenediamine (TMEDA) corresponding to 1 TMEDA per 52 C-Li, are added. Ethylene oxide (829g) is condensed into the reactor over a period of 90 minutes. Stirring is continued for 8 hours. After 24 hours the terminal lithoxy chain ends are converted to terminal hydroxy groups via the addition of a stoichiometric amount of $H_2O$. The resultant HTPB is then precipitated with methanol and stripped of residual solvent under vacuum. The analytical results are as follows:

|  | Theory | Found |
|---|---|---|
| Number Average Molecular Weight | 8000 | 8700 |
| OH No. (meq/g) | 0.25 | 0.23 |
| Functionality (OH) | 2.0 | 2.0 |
| Microstructure (IR) 1,2 (%) |  | 19 |
| 1,4 (%) |  | 81 |
| Yield (grams, %) |  | 3934,91 |
| Viscosity (Poise at 25° C) |  | 237 |
| Capping Efficiency (%) |  | 93 |

The contrast in capping efficiency by reason of the utilization of TMEDA is evidenced by a consideration of EXAMPLE 7 where TMEDA is not employed.

EXAMPLE 7

Preparation of an HTPB Employing a Difunctional Lithium Initiator with no TMEDA Added as Capping Catalyst EXAMPLE 6 is repeated except that 1765 ml of 0.89N DiLiDIPB in hexane, 113g THF, and 1380g ethylene oxide are employed. The resultant HTPB has the following properties:

|  | Theory | Found |
|---|---|---|
| Number Average Molecular Weight | 5000 | 4900 |
| Hydroxyl (OH) No. (meq/g) | 0.40 | 0.34 |
| Functionality (OH) | 2.0 | 1.67 |
| Microstructure 1,2 (%) |  | 22 |
| 1,4 (%) |  | 78 |
| Yield (grams, %) |  | 3352,85 |
| Viscosity (Poise at 25° C) |  | 57.9 |
| Capping Efficiency (%) |  | 85 |

EXAMPLE 8

Preparation of an HTPB Employing a Trifunctional Lithium Initiator and Using TMEDA as Capping Catalyst EXAMPLE 1 is repeated except that 30 liters of benzene, 3178g 1,3-butadiene, 2422 ml of 0.9N TriLi-DIPB solution of EXAMPLE 1 hereof, 156.9g THF (2.18 moles), 4.9g TMEDA (0.019 mole % based on Li) and 1918g ethylene oxide are employed. The resultant HTPB has the following properties:

|  | Theory | Found |
|---|---|---|
| Number Average Molecular Weight | 5000 | 5000 |
| OH No. (meq/g) | 0.60 | 0.50 |
| Functionality (OH) | 3.0 | 2.5 |
| Microstructure 1,2 (%) |  | 33 |
| 1,4 (%) |  | 67 |
| Yield (grams, %) |  | 2958,80 |
| Viscosity (Poise at 25° C) |  | 198 |
| Capping Efficiency (%) |  | 83 |

Again, the contrast in capping efficiency by reason of the utilization of TMEDA is evidenced by a consideration of EXAMPLE 9 where TMEDA is not employed.

EXAMPLE 9

Preparation of an HTPB Employing a Trifunctional Initiator with No TMEDA Added as Capping Catalyst EXAMPLE 1 is repeated except that 24 liters benzene, 2760 ml of 0.9N TriLi-DIPB solution, 178.6g THF and 2240g ethylene oxide are employed. The resultant HTPB has the following properties:

|  | Theory | Found |
|---|---|---|
| Number Average Molecular Weight | 5000 | 5500 |
| OH No. (meq/g) | 0.60 | 0.41 |
| Functionality | 3.0 | 2.18 |
| Microstructure 1,2 (%) |  | 30 |
| 1,4 (%) |  | 70 |
| Yield (grams, %) |  | 3326,83 |
| Viscosity (Poise at 25° C) |  | 30 |
| Capping Efficiency |  | 69 |

EXAMPLE 10

EXAMPLE 6 is repeated except that, instead of 2.12g TMEDA, 2.15g of N,N,N', N'-tetraethylethylenediamine are employed.

EXAMPLE 11

EXAMPLE 6 is repeated except that, instead of 2.12g TMEDA, 2.25g of N,N,N',N'-tetramethylpropylendiamine are employed.

EXAMPLE 12

EXAMPLE 8 is repeated except that, instead of 4.9g TMEDA, 5.4g of $(CH_3)_2$-N-$CH_2$-$CH_2$-O-$CH_3$ is employed.

EXAMPLE 13

Example 8 is repeated except that, instead of 4.9g TMEDA, 6.9g of $(C_2H_5)_2$-N-$CH_2$-$CH_2$-O-$CH_3$ is employed.

EXAMPLE 14

Example 8 is repeated except that, instead of 4.9g TMEDA, 8.7 of N,N,N', N'-tetraethylpropylenediamine is employed.

EXAMPLE 15

Preparation of a Hydroxy-Terminated Polybutadiene (HTPB) Employing a Trifunctional Lithium Initiator and TMEDA as Capping Catalyst 2724g of 1,3-butadiene and 20 liters of benzene are charged to a 10-gal polymerization reactor. A volume of 7260 ml (6.0 eq C-Li) of the 0.825N solution of the organotrilithium initiator of EXAMPLE 1 hereof are also added to the reactor. No precipitate occurs on addition of the initiator or during the ensuing 12-hour polymerization. The reactor and contents are cooled to −10° and 432g (6 moles) of THF along with 13.4g (0.115 moles) of TMEDA (corresponding to 1 TMEDA per 52 C-Li) are added. 2640g (60 moles) of ethylene oxide are then added to the carbonlithium containing polymer over a period of 2 hours while maintaining a reaction temperature of about −10°. After 24 hours the terminal lithoxy chain ends are converted to terminal hydroxy groups via the addition of a stoichiometric amount of $H_2O$. The resulting HTPB is then precipitated by addition of methanol and stripped of residual solvent under vacuum.

EXAMPLE 16

Preparation of a Hydroxyl-Terminated Polybutadiene Using a Mixed Organodi- and Trifunctional Initiator and TMEDA as Capping Catalyst Example 15 is repeated except that 3632g 1,3-butadiene, 24 liters benzene, 2205 ml 0.86N initiator solution (from EXAMPLE 2), 836g ethylene oxide and 4.23g TMEDA are employed.

EXAMPLE 17

Preparation of a Hydroxy-Terminated Polybutadiene Using a Mixed Organodi- and Trifunctional Initiator and TMEDA as Capping Catalyst Example 16 is repeated except that 1102g propylene oxide are employed.

We claim :

1. In a process for preparing hydroxy-terminated conjugated diene polymers and copolymers wherein the polymerization or copolymerization is carried out in the presence of at least one organopolylithium initiator, and wherein said polymers or copolymers having terminal polymer or copolymer C-Li bonds are capped with a lower alkylene epoxide capping agent, the improvement which consists in carrying out said capping reaction in the presence of a small proportion of a tertiary amine characterized by its having from 2 to 4 nitrogen atoms separated from each other by a saturated aliphatic hydrocarbon group containing from 2 to 8 carbon atoms or by a cycloaliphatic hydrocarbon group having from 4 to 8 carbon atoms.

2. The process of claim 1, in which the tertiary amine has the formulae:

$$\begin{array}{c} R'_1 \\ \diagdown \\ N-A-N \\ \diagup \\ R'_2 \end{array} \begin{array}{c} R'_3 \\ \diagup \\ \\ \diagdown \\ R'_4 \end{array} , \quad (CH_2)_x \begin{array}{c} CH_3 \\ \diagdown \\ N-A-N \\ \diagup \\ CH_3 \end{array} \begin{array}{c} CH_3 \\ \diagup \\ \\ \diagdown \\ CH_3 \end{array} (CH_2)_x ;$$

$$\text{I} \qquad\qquad \text{II}$$

$$\begin{array}{c} R'_1 \\ \diagdown \\ N-A-OR'_3 \\ \diagup \\ R'_2 \end{array}$$

$$\text{III}$$

wherein R'$_1$, R'$_2$, R'$_3$ and R'$_4$ are the same or different alkyl radicals of 1 to 4 carbon atoms, inclusive; x is an integer of 0 to 3, inclusive; and A in the formula is selected from the group consisting of: (1) cycloaliphatic and aromatic radicals and their lower alkyl derivatives having ring structures containing 5 to 7 members, wherein said radicals are attached to the nitrogen atoms at adjacent positions on the rings; (2) a monoethylenic radical, said radical containing 0 to 2 monovalent hydrocarbon radicals of 1 to 8 carbon atoms; and (3) 1 to 4 methylenic radicals, inclusive, wherein each methylenic radical contains 0 to 2 monovalent hydrocarbon radicals of 1 to 6 carbon atoms.

3. The process of claim 1, in which the tertiary amine corresponds to the formula $$\begin{array}{c} R'_1 \\ \diagdown \\ N-(CH_2)_n-N \\ \diagup \\ R'_2 \end{array} \begin{array}{c} R'_3 \\ \diagup \\ \\ \diagdown \\ R'_4 \end{array}$$

wherein $R'_1$, $R'_2$, $R'_3$ and $R'_4$ are the same or different alkyl radicals of 1 to 4 carbon atoms, inclusive; and $n$ is an integer between 1 and 4, inclusive.

4. The process of claim 1, in which the conjugated diene polymer is a 1,3-butadiene polymer having a molecular weight in the range of about 1,000 to about 15,000.

5. The process of claim 2, in which the conjugated diene polymer is a 1,3-butadiene polymer having a molecular weight in the range of about 1,000 to about 15,000.

6. The process of claim 3, in which the conjugated diene polymer is a 1,3-butadiene polymer having a molecular weight in the range of about 1,000 to about 15,000.

7. The process of claim 1, in which the tertiary amine comprises N,N,N',N'-tetramethylethylenediamine.

8. The process of claim 4, in which the teritary amine comprises N,N,N',N'-tetramethylethylenediamine.

9. The process of claim 5, in which the tertiary amine comprises N,N,N',N'-tetramethylethylenediamine.

10. The process of claim 6, in which the tertiary amine comprises N,N,N',N'-tetrapropylpropylenetriamine.

11. The process of claim 1, in which the intitiator is an organotrilithium compound in the form of a reaction product of (a) a mono-adduct of a disubstituted vinylic aromatic compound with an organodilithium compound with (b) a mono-alkyllithium compound.

12. The process of claim 1, in which the initiator is an organotrilithium compound in the form of a reaction product of (a) a mono-adduct of a disubstituted vinylic aromatic compound with a mono-alkyllithium compound with (b) an organodilithium compound; and in which the capping agent is a lower alkylene oxide.

13. The process of claim 3, in which the initiator is an organotrilithium compound in the form of a reaction product of (a) a mono-adduct of a disubstituted vinylic aromatic compound with a mono-alkyllithium compound with (b) an organodilithium compound; and in which the capping agent is a lower alkylene oxide.

14. The process of claim 3, in which the initiator is an organotrilithium compound in the form of a reaction product of (a) mono-adduct of diisopropenyl benzene with a $C_4$-$C_5$ secondary or tertiary alkyllithium compound with (b) an organodilithium compound; and in which the capping agent is a lower alkylene oxide.

15. The process of claim 6, in which the initiator is an organotrilithium compound in the form of a reaction product of (a) a mono-adduct of a disubstituted vinylic aromatic compound with a monoalkyllithium compound with (b) an organodilithium compound; and in which the capping agent is a lower alkylene oxide.

16. The process of claim 6, in which the initiator is an organotrilithium compound in the form of a reaction product of (a) a mono-adduct of diisopropenyl benzene with a $C_4$-$C_5$ secondary or tertiary alkyllithium compound with (b) an organodilithium compound; and in which the capping agent is a lower alkylene oxide.

17. The process of claim 9, in which the initiator is an organotrilithium compound in the form of a reaction product of (a) a mono-adduct of a disubstituted vinylic aromatic compound with a monoalkyllithium compound with (b) an organodilithium compound; and in which the capping agent is ethylene oxide.

18. The process of claim 9, in which the initiator is an organotrilithium compound in the form of a reaction product of (a) a mono-adduct of diisopropenyl benzene with a $C_4$-$C_5$ secondary or tertiary alkyllithium compound with (b) an organodilithium compound; and in which the capping agent is ethylene oxide.

19. The process of claim 9, in which the initiator is an organotrilithium compound in the form of a reaction product of 1,3-bis-(1-lithio-1,3-dimethylpentyl) benzene with 3-(1-lithio-1,3-dimethylpentyl)-alphamethylstyrene; and in which the capping agent is ethylene oxide.

20. The process of claim 9, in which the initiator is an organotrilithium compound in the form of a reaction product of a dilithio isoprene dimer with 3-(1-lithio-1,3-dimethylpentyl)-alphamethylstyrene; and in which the capping agent is ethylene oxide.

21. The process of claim 9, in which the initiator is an organotrilithium compound in the form of a reaction product of 1,3-bis-(1-lithio-3-methylpentyl) benzene and 3-(1-lithio-3-methylpentyl) styrene; and in which the capping agent is ethylene oxide.

22. The process of claim 9, in which the initiator is an organotrilithium compound in the form of a reaction product of sec-butyllithium with a mono-adduct of 1,3-bis-(1-lithio-1,3-dimethylpentyl) benzene with 1,3-diisopropenylbenzene; and in which the capping agent is ethylene oxide.

* * * * *